Figure 1:
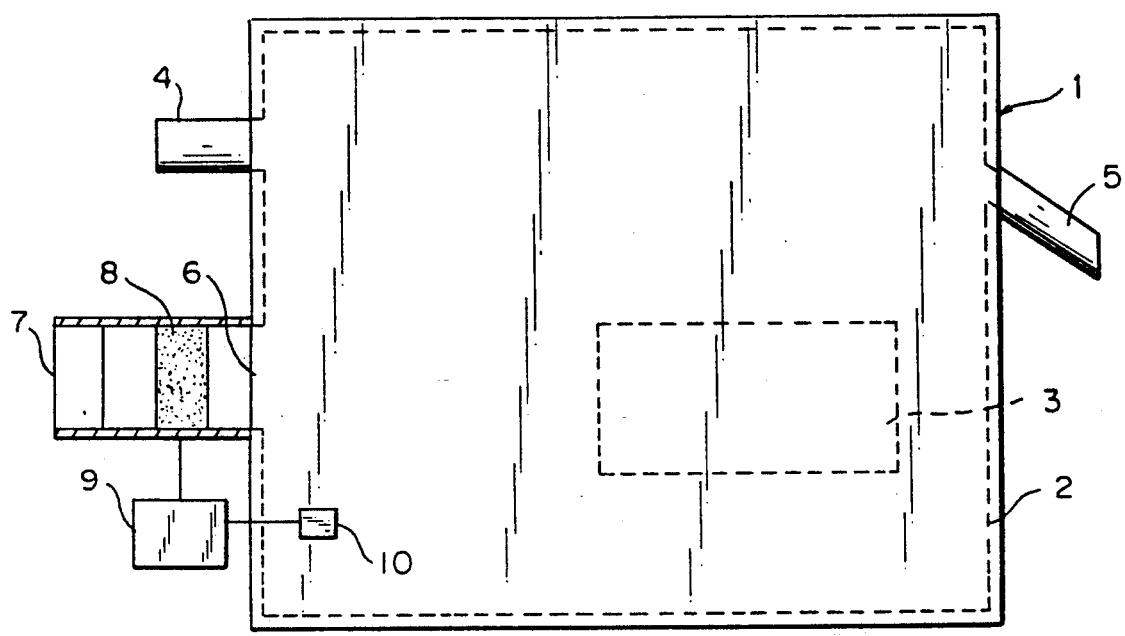

United States Patent
Rothstein et al.

[11] Patent Number: 5,293,753
[45] Date of Patent: Mar. 15, 1994

[54] METHOD FOR PREVENTING BACTERIAL GROWTH IN A FOOD PROCESSING PLANT AND SUCH A PLANT FOR CARRYING OUT THE METHOD

[75] Inventors: Sven-Olle Rothstein, Angelholm; Jan Solminger, Helsingborg, both of Sweden

[73] Assignee: Frigoscandia Food Process Systems AB, Helsingborg, Sweden

[21] Appl. No.: 854,600
[22] PCT Filed: Nov. 28, 1990
[86] PCT No.: PCT/SE90/00780
 § 371 Date: Jun. 9, 1992
 § 102(e) Date: Jun. 9, 1992
[87] PCT Pub. No.: WO91/07994
 PCT Pub. Date: Jun. 13, 1991

[30] Foreign Application Priority Data
Nov. 29, 1989 [SE] Sweden ............... 8904041-4

[51] Int. Cl.⁵ ................................. F24F 3/16
[52] U.S. Cl. .......................... 62/78; 62/440; 165/2; 165/58
[58] Field of Search ............ 62/78, 440; 165/2, 58

[56] References Cited
U.S. PATENT DOCUMENTS
3,891,779  6/1975  Robinson ............... 426/399
4,845,958  7/1989  Senda et al. ............ 62/78
5,077,009  12/1991  Subotics et al. ......... 62/78

FOREIGN PATENT DOCUMENTS
0151735  8/1985  European Pat. Off.
2403061  7/1975  Fed. Rep. of Germany.
2919695  11/1980  Fed. Rep. of Germany.
444890   2/1984  Sweden.

Primary Examiner—Ronald C. Capossela
Attorney, Agent, or Firm—Browdy and Neimark

[57] ABSTRACT

In a method for preventing bacterial growth in a refrigerating or freezing plant for food, the plant (1) includes a substantially closed housing (2) and, arranged therein, a device (3) for refrigerating food in this housing, and has an operating cycle including a work period during which the refrigerating device (3) is active, and a rest period during which the refrigerating device (3) is inactive and the plant can be cleaned. The cleaning includes raising the temperature in the plant above a temperature requisite for killing bacteria. Furthermore, the air pressure in the plant is maintained higher than the ambient pressure, at least during the entire rest period, by supplying air free from bacteria. The plant (1) includes heaters for raising the temperature therein during a rest period above a temperature requisite for killing bacteria, and air supply devices (7, 8) for supplying the air free from bacteria.

20 Claims, 3 Drawing Sheets

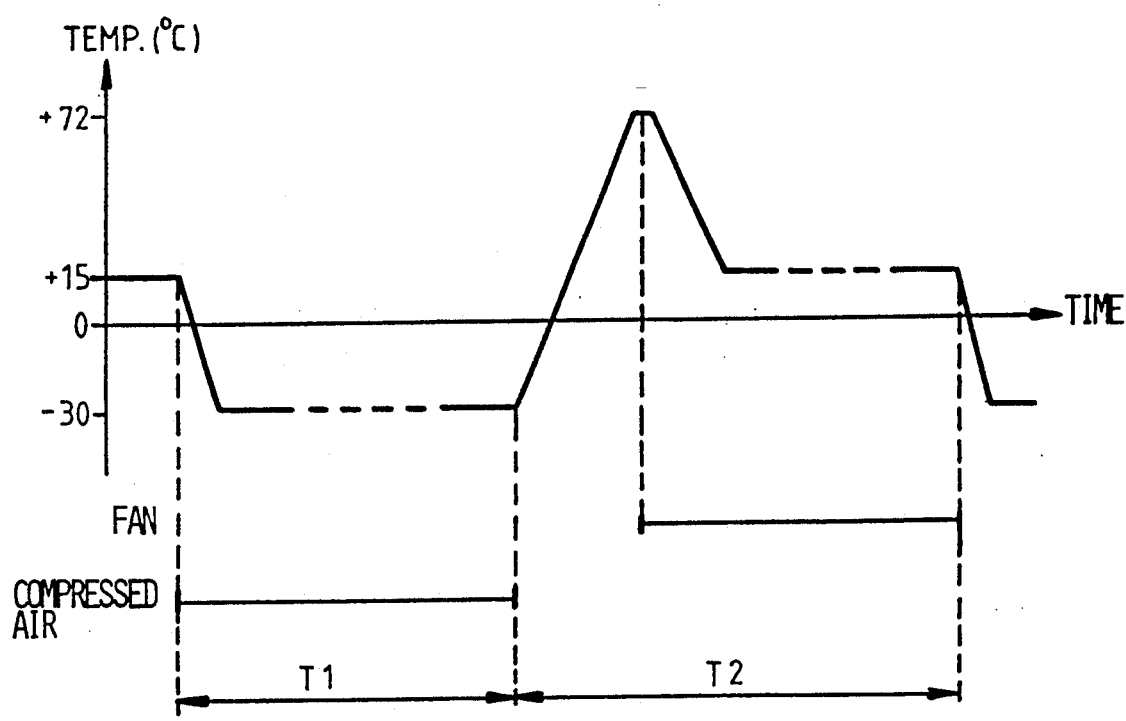

METHOD FOR PREVENTING BACTERIAL GROWTH IN A FOOD PROCESSING PLANT AND SUCH A PLANT FOR CARRYING OUT THE METHOD

This invention generally relates to a refrigerating or freezing plant for food, said plant comprising a substantially closed housing and, arranged therein, means for refrigerating food in said housing, and having an operating cycle which comprises a work period during which the refrigerating means are active, and a rest period during which the refrigerating means are inactive and the plant can be cleaned. More precisely, the invention concerns a method for preventing bacterial growth in such a plant, as well as a refrigerating or freezing plant for carrying out the inventive method.

At regular intervals, plants for refrigerating or freezing food on an industrial scale must be completely cleaned to remove any remaining food and prevent bacterial growth. In most cases, this is achieved by switching off the plant, which then is manually cleaned with suitable detergents and hot water. Alternatively, the plant can be cleaned by means of a fixedly mounted piping system having spray nozzles through which the detergents and the hot water are supplied.

The effect of such cleaning has, however, proved to be comparatively short-lived. When the plant is to be started up again, the temperature therein is, of course, reduced. This reduction in temperature is followed by a reduction in pressure, resulting in that air which may contain bacteria is drawn into the plant from the surrounding atmosphere. Also occasional pressure reductions during operation may entail the ingress of bacteria.

One object of the invention is, therefore, to provide a refrigerating or freezing plant preventing, or at least reducing the risk of, bacterial growth, especially upon the reductions in temperature and pressure taking place when the refrigerating means are reactivated. Another object of the invention is to provide a method for preventing bacterial growth in such a refrigerating or freezing plant for food.

According to the invention, the first-mentioned object is achieved by a refrigerating or freezing plant of the type mentioned in the introduction to this specification, which is characterised by means for raising the temperature in the plant, during a rest period, above a temperature requisite for killing bacteria, e.g. 72° C., and means for supplying air free from bacteria to the interior of the plant in order to raise the air pressure therein above the ambient pressure, at least during the entire rest period, said air supply means comprising a fan which communicates with an opening in the housing of the plant and is adapted to supply air for as long as the temperature in the housing is above a given temperature, e.g. 0° C.

Advantageously, the air supply means further comprises an air compressor which is connected in series to a compressed-air container having an air outlet disposed in the plant.

The second-mentioned object of the invention is achieved in that the cleaning includes raising the temperature in the plant above a temperature requisite for killing bacteria, preferably 72° C., and that the air pressure in the plant is maintained higher than the ambient pressure, at least during the entire rest period, by supplying air free from bacteria by means of a fan for as long as the temperature in the housing is above a given temperature, e.g. 0° C.

According to the invention, the air pressure in the plant is suitably maintained higher than the ambient pressure also during the work period by supplying air free from bacteria.

By air free from bacteria is meant both air which has been rid of bacteria, e.g. by filtering, and air in which the bacteria have been killed, e.g. by heating.

Figure 2:
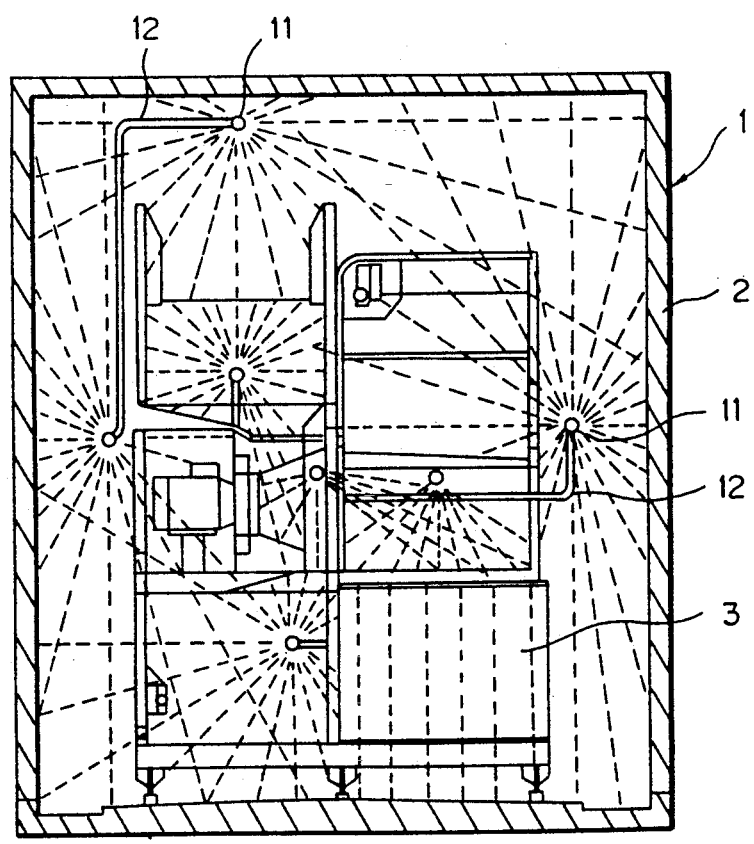
Figure 3:
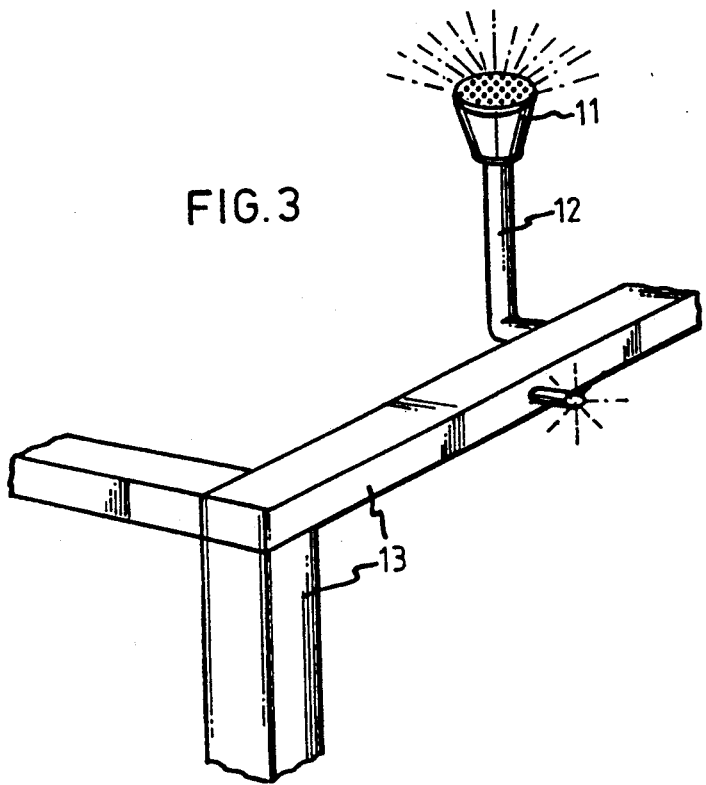
Figure 4:
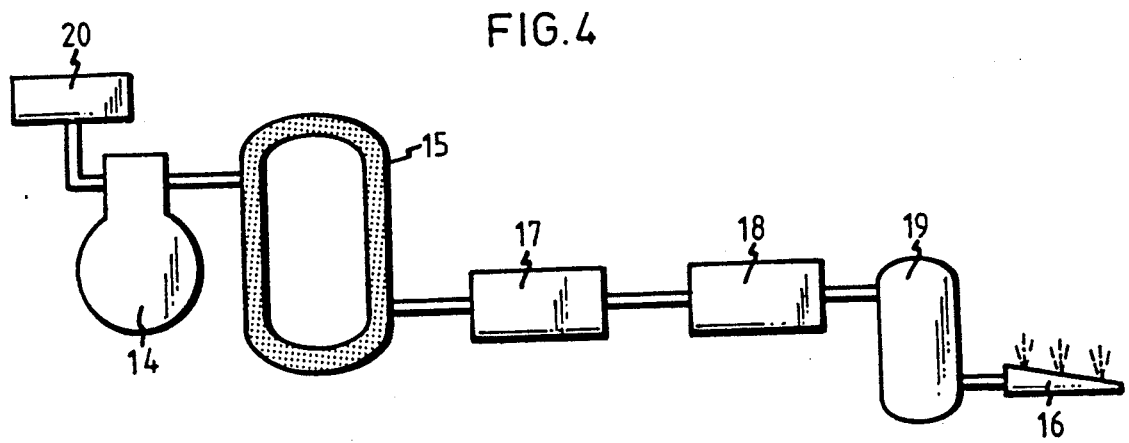

The invention will be described in more detail below, reference being had to the accompanying drawings, in which FIG. 1 is a schematic view of a freezing plant according to the invention, FIG. 2 is a cross-section of the inventive freezing plant, FIG. 3 is a perspective view of part of the plant in FIG. 2, FIG. 4 is a schematic view of a preferred embodiment of a subsystem of the inventive freezing plant, and FIG. 5 schematically illustrates an operating cycle of the inventive freezing plant.

The invention is applicable to all refrigerating and freezing plants for food which comprise a substantially closed housing and, arranged therein, means for refrigerating the food in the housing. U.S. Pat. No. 3,886,762 and U.S. Pat. No. 3,938,651 disclose such freezing plants.

FIG. 1 schematically illustrates a freezing plant 1 which comprises a housing 2 containing means 3, e.g. a cooling-coil battery or spray nozzles for a refrigerant, for refrigerating food in the housing 2. The housing is substantially closed, but has an infeed opening 4 and an outfeed opening 5 for the food which is to be processed in the freezing plant.

According to the invention, the housing 2 of the plant 1 is formed with an additional opening 6 to which a fan 7 and an air filter 8 are connected in series. The motor of the fan 7 is connected to a control unit 9 which in turn is connected to a pressure transducer 10 disposed in the housing 2.

For cleaning, the freezing plant shown in FIG. 1 operates as follows. When the plant has been emptied of food, the refrigerating means 3 are inactivated, and defrosting begins. This may be accelerated by heating the interior of the freezing plant, e.g. by flushing hot vapour or hot water, or by blowing hot air. When defrosting is completed, cleaning begins, which means that the interior of the plant is manually or automatically flushed or rinsed with a suitable detergent by means of fixedly mounted equipment, whereupon it is flushed or rinsed with hot water. Naturally, this increases the temperature in the housing 2 of the freezing plant 1, and the temperature is, after or during cleaning, further increased by means of vapour or hot water to above a temperature requisite for killing bacteria, preferably above 72° C., for a minimum time, e.g. 15 s. In this manner, all the bacteria in the plant are killed.

When the freezing plant is to be started up again, the temperature in the housing 2 must be lowered to normal working temperature, which is done by the refrigerating means 3. Before or at the same time as the refrigerating means 3 are activated, the fan 7 is actuated to blow air, which thanks to the filter 8 is free from bacteria, through the opening 6 into the housing 2. Thus, the air pressure in the housing 2 is raised above the ambient pressure. The pressure transducer 10 and the control unit 9 are used for maintaining the positive pressure in the housing 2 at a suitable level. The control unit 9 controls the motor of the fan 7 as a function of signals from the pressure transducer 10 indicating the pressure in the housing 2. The positive pressure in the housing 2 is maintained during the entire cooling to normal working temperature. When this temperature has been achieved, the fan 7 is stopped and the freezing plant 1 is in running order.

By raising the air pressure in the plant with air free from bacteria during the cooling, air is prevented from being drawn into the plant through the infeed and outfeed openings 4 and 5, as well as through leaks, if any, in the housing 2.

With the above embodiment of the invention, the bacterial growth in a freezing plant may thus be much delayed, thereby considerably prolonging the operating time between cleanings.

FIG. 2 illustrates an embodiment of a spray equipment which is fixedly mounted in a freezing plant and adapted to sprinkle both detergent and hot water over all the free surfaces inside the plant. The spray equipment comprises a plurality of suitably positioned spray nozzles 11 mounted on conduits 12 through which the detergent and the hot water are pumped to the spray nozzles 11 from sources outside the refrigerating plant 1.

According to the invention, this cleaning equipment may advantageously be used for raising the temperature in the plant 1 above the temperature required for killing bacteria. For this purpose, hot water or even vapour can be used. As is obvious to anyone skilled in the art, it is also possible to increase the temperature in the plant by other means.

Frequently, the equipment in a freezing plant is mounted on a frame of tubular sections. Of course, it is difficult to clean these sections on the inside, and there is a risk of uncontrolled bacterial growth therein. In an especially preferred embodiment of the invention, this inconvenience is obviated by the tubular sections, e.g. the tubular sections 13 in FIG. 3, being part of the conduits 12 in FIG. 2 for supplying detergent and hot water to the spray nozzles 11. Thus, also the interiors of the tubular sections 13 forming the frame supporting the equipment in the plant 1 are completely cleaned and all the bacteria therein killed.

To prevent all bacterial growth in a refrigerating or freezing plant, the air pressure in the plant must be maintained higher than the ambient pressure during the entire operating cycle, i.e. during both the work period and the rest period. Since the fan 7 and the filter 8, at least in a freezing plant of the type described above, are not suited for supplying air when the temperature in the plant falls below a given temperature, e.g. 0° C., the most preferred embodiment of the invention comprises supplementary means adapted to supply air free from bacteria, when the temperature in the plant goes below the given temperature.

FIG. 4 illustrates such a supplementary means which, more precisely, comprises a compressor 14 feeding a compressed-air container 15 which in turn communicates with an air outlet 16 arranged in the housing 2 in the form of one or more compressed-air nozzles. The air outlet 16 may simultaneously serve to remove frost from the surface of a cooling-coil battery forming part of the refrigerating means 3. In that case, the air outlet is usually mounted in such a manner that it can move back and forth over the cooling-coil battery to remove frost from the surface thereof. The intake air of the compressor 14 normally comes from the air surrounding the freezing plant 1, and bacteria may thus be admitted to the interior of the plant 1 via the outlet 16. In order to obviate this risk, the container 15 may be heat-insulated and contain electric equipment for heating the air in the container 15 to a temperature sufficiently high to kill any bacteria in the air. Then, the compressed air is conducted, via a cooler 17 and a drier 18, to another compressed-air container 19 which, however, only is necessary if the air outlet 16 is used for defrosting.

As an alternative to the heating in the container 15, the compressor 14 may, on the intake side, be connected to a bacteria-intercepting filter.

FIG. 5 schematically illustrates an operating cycle for the most preferred embodiment of the inventive freezing plant. More precisely, it shows the variation of temperature in the plant, and the activation periods for the fan 7 and the compressed-air assembly 14–18.

The operating cycle comprises a work period T1 during which the refrigerating means 3 are activated, and a rest period T2 during which these means are inactivated or switched off. At the end of a rest period, the temperature in the plant may be e.g. 15° C. The fan 7 is then used for maintaining the positive pressure in the plant.

The work period T1 begins with activation of the refrigerating means 3, causing the temperature in the plant to decrease and finally reach a working temperature of e.g. −30° C. Simultaneously with activation of the refrigerating means 3, or when the temperature in the plant passes e.g. 0° C., the fan 7 is disconnected and the compressed-air assembly 14–18 is activated. Usually, this is achieved by opening a valve (not shown) situated immediately ahead of the nozzles 19, since working pressure is normally maintained at all times in the container 15 by the compressor 14.

The fan 7 cannot be used at the working temperature of the plant, because of the risk of frost formation which would prevent the filter 8 and the fan 7 from functioning. According to the invention, it is therefore preferred that the opening 6 is closed in such a manner that the filter 8 and the fan 7 are not exposed to the low working temperature in the plant when the fan 7 is not in use.

The work period T1 is ended by disconnection of the refrigerating means 3. Then, the temperature in the plant increases, and defrosting begins. The rate of increase may be accelerated by flushing the interior of the plant with hot water which also cleans it. According to the invention, the temperature in the plant is then raised to the requisite temperature, e.g. at least 72° C., for killing bacteria.

During the time interval between disconnecting the refrigerating means 3 and reaching e.g. 72° C., no air need be supplied to the plant in order to maintain a positive pressure therein.

As soon as the temperature increase in the plant ceases, the fan 7 is activated to maintain a positive pressure in the plant during the remainder of the rest period T2. The temperature in the plant decreases and stabilises at e.g. 15° C. At the next changeover from rest period to work period, the above procedure is repeated.

It goes without saying that the invention is not restricted to the embodiments described above, which of course may be modified in many ways by the expert.

We claim:

1. A method for preventing bacterial growth in a refrigerating or freezing plant for food, said plant (1) comprising a substantially closed housing (2) and, arranged therein, refrigerating means (3) for refrigerating food in said housing, comprising:

activating said refrigerating means for a work period (T1) to refrigerate or freeze food; and inactivating said refrigeration means and cleaning said plant during a rest period (T2), wherein said cleaning includes raising the temperatures in the plant above a temperature requisite for killing bacteria and maintaining air pressure in the plant higher than the ambient pressure, at least during the entire rest period, by supplying air free from bacteria within said plant.

2. The method of claim 1, further comprising maintaining the air pressure in the plant is maintained higher than the ambient pressure also during the work period by supplying air free from bacteria.

3. The method of claim 1, comprising filtering the air with a bacteria-intercepting filter (8).

4. The method of claim 1, further comprising raising the temperature during said rest period by spraying the interior of the plant with vapour or water of a temperature higher than the requisite for killing bacteria.

5. A method according to claim 1 wherein said raising the temperature in the plant above a temperature requisite for killing bacteria comprises raising the temperature to at least 72° C.

6. A method according to claim 1 wherein said maintaining of said air pressure in said plant higher than ambient pressure is carried out as long as the temperature in the housing is above 0° C.

7. A method for preventing bacterial growth in a refrigerating or freezing plant for food, said plant (1) comprising a substantially closed housing (2) and, arranged therein, refrigerating means (3) for refrigerating food in said housing, comprising:

activating said refrigerating means for a work period (T1) to refrigerate or freeze food; and inactivating said refrigeration means and cleaning said plant during a rest period (T2), wherein said cleaning includes raising the temperatures in the plant above a temperature requisite for killing bacteria and maintaining air pressure in the plant higher than the ambient pressure, at least during the entire rest period, by supplying air through a bacteria-intercepting filter (8) within said plant via a compressed-air container (15) and exhaust nozzles (16) arranged in the plant (1).

8. The method of claim 7, further comprising defrosting the refrigerating means (3) during said rest period using said exhaust nozzles (16).

9. The method of claim 8, further comprising raising the temperature during said rest period by spraying the interior of the plant with vapour or water of a temperature higher than the requisite for killing bacteria.

10. A plant for refrigerating or freezing food, comprising a substantially closed housing (2) and, arranged therein, means (3) for refrigerating food in said housing, and having an operating cycle which comprises a work period (T1) during which the refrigerating means (3) are active, and a rest period (T2) during which the refrigerating means (3) are inactive and the plant can be cleaned, means (11, 12) for raising the temperature in the plant (1) during a rest period (T2) above a temperature requisite for killing bacteria, and air supply means (7, 8, 14–18) for supplying air free from bacteria to the interior of the plant in order to raise the air pressure therein above the ambient pressure, at least during the entire rest period (T2), said air supply means comprising a fan (7) which communicates with an opening (6) in the housing (2) of the plant for supplying air for as long as the temperature in the housing is above a given temperature.

11. The plant of claim 10, wherein said the fan (7) communicates in series with a bacteria-intercepting air filter (8).

12. The plant of claim 10, further comprising a pressure transducer (10) mounted in the plant, and a control means (9) connected thereto for controlling the air supply means (7, 8, 14–18) in such a manner that a positive pressure relative to the ambient pressure is maintained during the entire operating cycle of the plant.

13. The plant of claim 10, wherein said the means (11, 12) for raising the temperature in the plant comprise a system for spraying hot vapour or hot water.

14. The plant of claim 13, wherein said the spray system (11, 12) comprises a plurality of spray nozzles (11), and conduits (12) for conveying water to said nozzles and forming part of a frame (13) in the housing (2).

15. A plant for refrigerating or freezing food, comprising a substantially closed housing (2) and, arranged therein, means (3) for refrigerating food in said housing, and having an operating cycle which comprises a work period (T1) during which the refrigerating means (3) are active, and a rest period (T2) during which the refrigerating means (3) are inactive and the plant can be cleaned, means (11, 12) for raising the temperature in the plant (1) during a rest period (T2) above a temperature requisite for killing bacteria, and air supply means (7, 8, 14–18) for supplying air free from bacteria to the interior of the plant in order to raise the air pressure therein above the ambient pressure, at least during the entire rest period (T2), said air supply means comprising a fan (7) which communicates with an opening (6) in the housing (2) of the plant for supplying air for as long as the temperature in the housing is above a given temperature, wherein the air supply means comprise an air compressor (14) which is connected in series to a compressed-air container (15) having an air outlet (16) disposed in the plant.

16. The plant of claim 15, further comprising control means for disconnecting the fan (7) and connecting the air compressor (14) upon changeover from a rest period (T2) to a work period (T1).

17. The plant of claim 15, wherein the air outlet (16) comprises a plurality of exhaust nozzles for removing frost from the refrigerating means (3).

18. The plant of claim 17 further comprising a pressure transducer (10) mounted in the plant, and a control means (9) connected thereto for controlling the air supply means (7, 8, 14–18) in such a manner that a positive pressure relative to the ambient pressure is maintained during the entire operating cycle of the plant.

19. The plant of claim 18 wherein said means (11, 12) for raising the temperature in the plant comprise a system for spraying hot vapor or hot water.

20. The plant of claim 19, wherein said fan (7) communicates in series with a bacteria-intercepting air filter (8).

* * * * *